United States Patent [19]

McLees

[11] Patent Number: 5,092,875
[45] Date of Patent: Mar. 3, 1992

[54] BONE SAW FOR TENDON TRANSPLANT SURGERY

[76] Inventor: Donald J. McLees, 2623 Virginia Ave., Everett, Wash. 98201

[21] Appl. No.: 516,356

[22] Filed: Apr. 30, 1990

[51] Int. Cl.⁵ .............................................. A61B 17/14
[52] U.S. Cl. ....................................... 606/178; 606/82
[58] Field of Search ...................... 606/79, 80, 81, 82, 606/176, 177, 178, 179; 30/166.3, 389

[56] References Cited

U.S. PATENT DOCUMENTS

| | | | |
|---|---|---|---|
| 493,730 | 3/1893 | MacKenzie | 606/179 |
| 3,269,010 | 4/1964 | Bettcher | 30/316 |
| 4,409,973 | 10/1983 | Neuffield | 606/179 |
| 4,596,243 | 6/1986 | Bray | 606/79 |
| 4,708,133 | 11/1987 | Comparetto | 606/177 |
| 4,768,504 | 9/1988 | Ender | 606/178 |
| 4,936,313 | 6/1990 | Burkhardt et al. | 606/180 |
| 4,955,888 | 9/1990 | Slocum | 606/178 |

Primary Examiner—John D. Yasko
Assistant Examiner—William W. Lewis

[57] ABSTRACT

A power saw for cutting the bone plug portions of a tendon graft which is to be transplanted. The saw blade is a circular ring of teeth which is oscillated about the circle center by a peripheral drive, thereby enabling circular bone plugs to be cut and eliminating the need to manually trim the bone plugs to an approximately circular cross section.

2 Claims, 3 Drawing Sheets

BONE SAW FOR TENDON TRANSPLANT SURGERY

BACKGROUND OF THE INVENTION

One of the most common knee surgeries currently being performed is the anterior cruciate ligament transplant. In this operation the anterior cruciate ligament is replaced by a graft from the patient's patellar tendon. The graft includes bone plugs at both ends of the tendon which are typically removed from the patient's own patella and tibia using a hammer and chisel and perhaps also a standard reciprocating saw. The bone plugs of the resultant graft must then be trimmed to an approximate circular cross section of typically either 9 millimeters or 10 millimeters in diameter for insertion into drilled out femoral and tibial tunnels.

Since the chiseled bone plugs are approximately triangular or rectangular in cross section and the desired plugs are to be circular, obviously more bone must be removed from the patient than if the means were available to cut a circular cross section plug from the donor site to begin with. Also the bone trimming process can be tedious and inexact and also quite costly since the patient must remain under anesthesia and the remainder of the operating team must stand by as one person trims the bone plugs. More time is lost if the bone plugs must be re trimmed after the initial attempt at insertion into the transplant site. Clearly a substantial improvement to this operation could be realized if a tool were available to initially cut properly sized circular cross section plugs from the donor sites.

Attempts have been made to use a conventional hole saw for cutting the plugs, but the results have not been satisfactory. A conventional hole saw cannot easily cut out a plug which must be parallel to and congruent with the surface of the bone because of the presence of the hole saw shaft. The proper entry angle could only be achieved if the bone portion opposite to the direction of the cut were first removed. This is an unsatisfactory solution since the patient is also the donor and it becomes therefore quite important to conserve intact as much of the donor's bone as possible. What is needed is a shaftless hole saw, which is the object of this invention.

Figure 2:
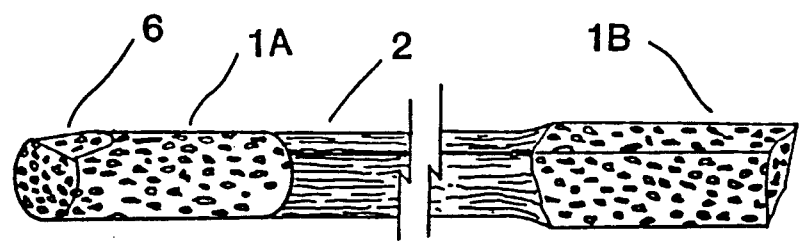

A graft consisting of a chiseled bone section, a portion of the patellar tendon, and a bone plug as cut out by the bone saw is shown isometrically in FIG. 2.

Figure 3:
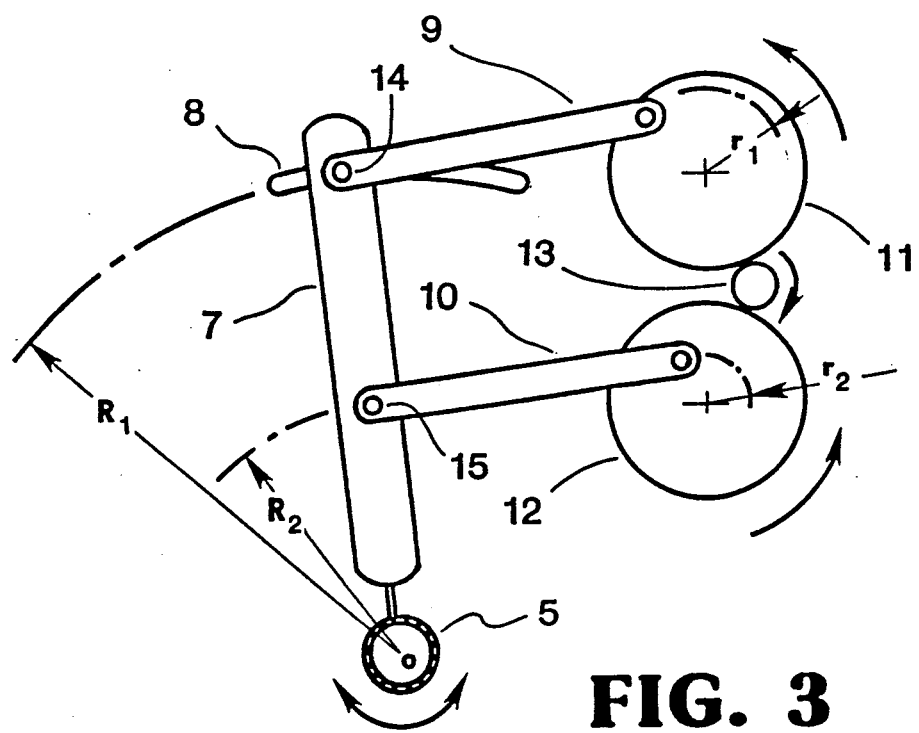

FIG. 3 is a front view diagram of one preferred embodiment of the saw mechanism.

Figure 4:
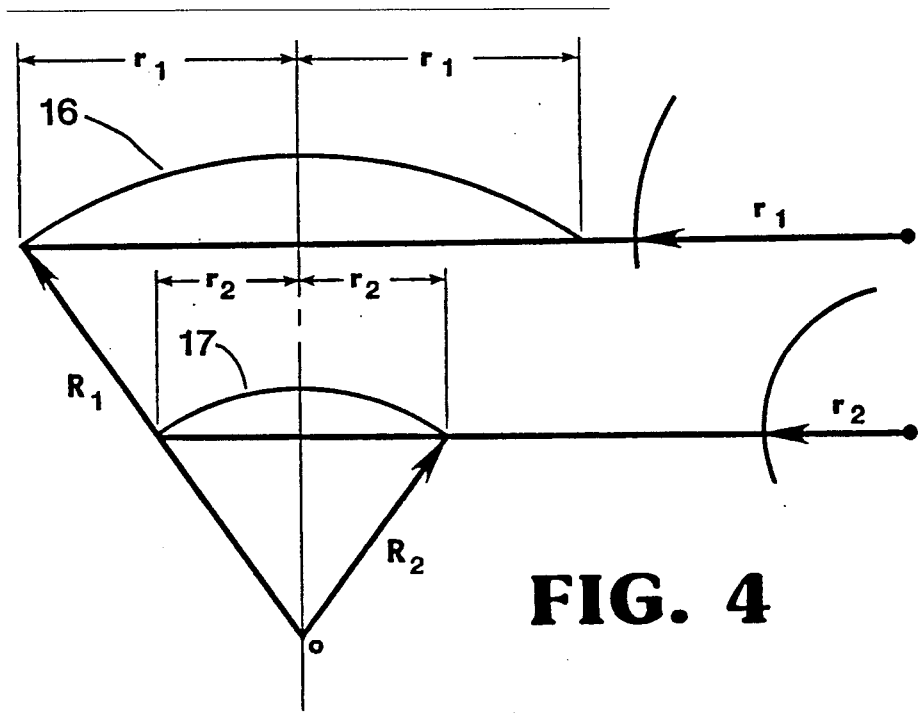

FIG. 4 shows the geometry of the motion of the mechanical elements diagramed in FIG. 3.

Figure 5:
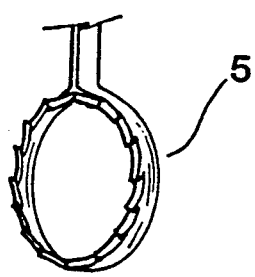

FIG. 5 is an isometric of the saw blade.

DETAILED DESCRIPTION OF THE DRAWINGS

Figure 1:
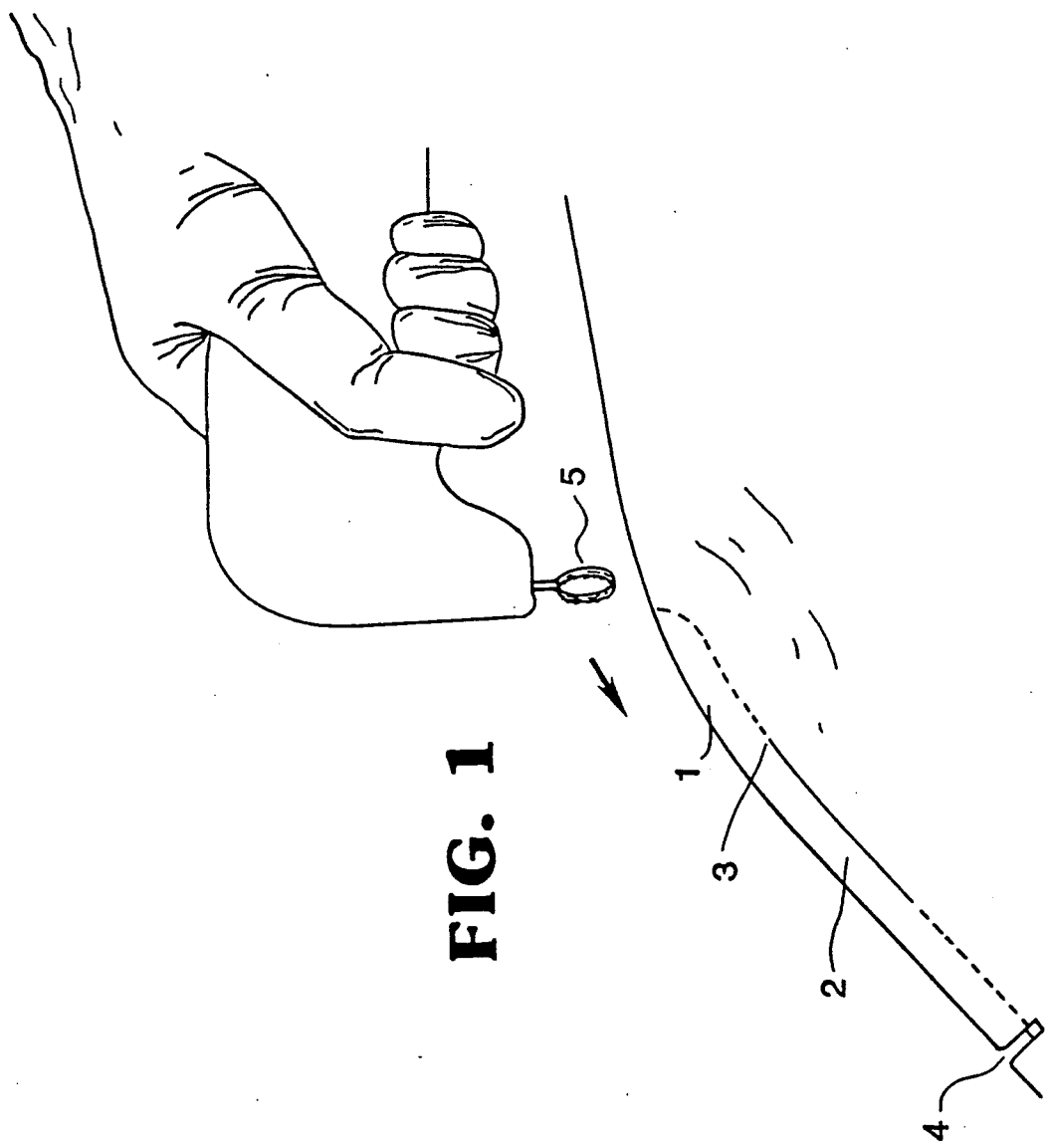
FIG. 1 is a side view diagram showing how the saw would be used in knee ligament transplant surgery.

FIG. 1 diagrams the approximate location of the intended cuts and shows the approximate size of the patellar (kneecap) bone plug 1 in relation to the saw blade 5. The dashed line indicates the approximate path of the saw cut. The point 3 at which the dashed line ends and the solid line begins indicates the beginning of the tendon portion 2 of the graft, the solid line showing where a slice would be made to separate the graft portion 2 from the remaining portion of the patellar tendon. The saw blade 5 is moved in the direction of the arrow to cut the plug until the end of the patella at 3 is reached. At that point the saw blade is backed out opposite the arrow direction while the saw is kept running to aid removal.

The procedure using the bone saw may require that a slot 4 first be cut in the bone (in this example the tibia) to allow entry of the saw blade. The slot can be cut by a standard reciprocating bone saw or, to be more efficient and preserve more of the donor bone intact, by a special slot cutter which would cut the slot slightly wider than the bone saw width and slightly longer and deeper than the saw blade diameter. Once the slot is cut the bone saw blade can be inserted to the desired depth and then moved opposite the direction of the arrow of FIG. 1 to cut the plug.

If the saw blade is inserted to a depth such that the top of the blade is right at the surface of the bone and remains at that depth as the cut is made, a plug of completely round cross section along its length will result. However, the surgeon does have the option of either beginning the cut with the top of the blade slightly above the bone and then moving the blade down into the bone as the cut proceeds, or of beginning the cut with the top of the blade at the surface of the bone and then moving the top of the blade up and slightly out of the bone as the blade approaches the patellar tendon. This would result in a plug of mostly circular cross section, but with a flat side at either the proximal or distal end of the plug. The flat side facilitates insertion of a screw which anchors the plug in the drilled out tunnel at the location of the transplant. Such a plug having a flat side 6 is shown in FIG. 2.

As with the patellar plug, when the tibial cut reaches the patellar tendon the saw is backed out while still running and removed through the slot. The bone plug can then be pushed out and the graft removed.

A typical chiseled bone piece 1B is shown at the right end of a graft in FIG. 2. Since the bone plug must fit into a round tunnel while maintaining as high a percentage of surface area as practical in contact with the tunnel wall in order to receive oxygen and nutrients from the surrounding bone, the chiseled piece 1B must be manually rounded off, resulting in a bone plug that is an approximation of a cylindrical piece of bone at best. At the other end of the portion of patellar tendon 2 shown in FIG. 2 however is a bone plug 1A as it would appear after being separated from the donor site by the bone saw, requiring no further manual modification and being of essentially the exact required shape and diameter. The particular bone plug illustrated has been cut by the method described above in the detailed description of FIG. 1, leaving a flat side 6 at the distal end to facilitate anchor screw insertion.

The mechanism diagramed in FIG. 3 represents one possible embodiment of the invention. Various alternative drives are capable of producing the desired reciprocating rotational motion of the circular saw blade 5 about its axis (0 of FIGS. 3 and 4) as long as those alternative mechanisms constrain the motion of all points on any member rigidly affixed to the saw blade (such as arm 7 of FIG. 3) to arcs of concentric circles having the blade center 0 as their center.

The basic elements of the preferred embodiment of the invention diagramed in FIG. 3 include the arm 7 rigidly affixed to the saw blade 5, a guide slot 8, two links 9 and 10, two driven gears 11 and 12, and drive gear 13. The drive gear 13 can be rotated by a commonly available pneumatic or electric surgical power head. Since the drive gear is in mesh with identical driven gears 11 and 12, the driven gears must rotate at the same speed in the direction indicated by the arrows of FIG. 3. Link 10 is pinned at one end to gear 12 at a distance $r_2$ from the gear center and at the other end to arm 7 at a distance $R_2$ from the geometric center 0 of blade 5. Link 9 is pinned at one end to gear 11 at a distance $r_1$ from the gear center and at the other end to arm 7 at a distance $R_1$ from the geometric center of the blade. The link 9 arm pin 14 extends through slot 8 which is concentric with the blade center. The dimensions and locations of the elements are chosen such that the pinned Joint 15 connecting link 9 to arm 7 is also constrained to reciprocating semi-circular motion about the blade center.

The geometry of the mechanism of FIG. 3 is shown in FIG. 4. The motion of pin 14 (arc 16 of FIG. 4) is constrained by slot 8 to a semi-circular arc having the same center as the saw blade. Since the center of gear 11 lies on the same line as the endpoints of the arc circumscribed by pin 14 (16 of FIG. 4) and the center of gear 12 lies on the same line as the endpoints of the arc circumscribed by pin 15 (17 of FIG. 4), and since the mechanism is synchronized so that both pins reach the end of arc travel simultaneously, and also since $r_1/r_2 = R_1/R_2$, pin 15 is necessarily constrained to similar semi-circular motion about the blade center (arc 17 of FIG. 4). Since two separate points (pins 14 and 15) on arm 7 must reciprocate in semi-circular arcs about the blade center 0, and since arm 7 is rigidly attached to the blade 5, the blade itself is forced to oscillate about its own center and thus the mechanism satisfies the objective of the invention. It is a peripherally driven circular hole saw which, since it has no shaft at the center of rotation, can be inserted into a small slot and can then cut out a cylindrical plug. FIG. 5 shows the saw blade in isometric detail.

Geometrically, any alternative mechanism must work in one of two possible ways. It can either constrain two or more points to semi-circular motion as does the mechanism of FIGS. 3 and 4 or it can constrain one point to semi-circular motion while rotating that same point at such a rate that the center of the saw blade remains at the same location.

While this invention was initially conceived to improve cruciate ligament transplant surgery, it need not be limited to that particular application. It can be used to cut a cylindrical piece from any bone or it can be used to cut cylinders or rods from any other material with the advantage over a conventional hole saw of being unrestricted as to the length of the cut which can be made.

What is claimed is:

1. A shaftless rotary oscillating surgical bone saw comprising:
    a ring in operative combination with a peripherally attached drive arm, said ring having a plurality of axially oriented teeth protruding from one end, said ring being supported only by said arm and thereby said ring being capable of being inserted into a bone slot which is slightly wider than the ring width to a depth equal to the ring diameter, said ring being completely opened at both ends and thereby allowing a cylindrical bone plug of unrestricted length to be cut; and
    reciprocating drive means constraining two separate points on said drive arm to reciprocating motion along semi-circular arcs of concentric circles which have the axis of the ring as their center, said drive means thereby causing said ring of teeth to rotationally reciprocate about its axis.

2. A shaftless rotary oscillating surgical bone saw comprising:
    a ring in operative combination with a peripherally attached drive arm, said ring having a plurality of axially oriented teeth protruding from one end, said ring being supported only by said arm and thereby said ring being capable of being inserted into a bone slot which is slightly wider than the ring width to a depth equal to the ring diameter, said ring being complete opened at both ends and thereby allowing a cylindrical bone plug of unrestricted length to be cut, and
    reciprocating drive means constraining a point on said drive member to reciprocating motion along a semi-circular arc of a circle which has the axis of said ring as its center, said drive means also causing said point to rotate such that the center of the ring remains stationary, said drive means thereby causing said ring of teeth to rotationally reciprocate about its axis.

* * * * *